United States Patent [19]

Acher et al.

[11] Patent Number: 5,116,859

[45] Date of Patent: * May 26, 1992

[54] METHOD OF PROVIDING ANXIOLYTIC AND ANTIPSYCHOTIC TREATMENT

[75] Inventors: Jacques Acher, Itteville; Jean-Claude Monier, Lardy; Jean-Paul Schmitt, Arpajon, all of France; Brenda Costall; Robert Naylor, both of Ilkey, United Kingdom; Renee Gardaix-Luthereau, Cachan, France

[73] Assignee: Laboratoires Delagrance Societe d'Application Pharmacodynamiques, Paris Cedex, France

[*] Notice: The portion of the term of this patent subsequent to Oct. 26, 2007 has been disclaimed.

[21] Appl. No.: 207,947

[22] Filed: Jun. 17, 1988

[30] Foreign Application Priority Data

Jun. 17, 1987 [EP] European Pat. Off. ......... 87401364.2

[51] Int. Cl.$^5$ ............................................. A01M 43/50
[52] U.S. Cl. ....................................... 514/392; 514/810; 514/811; 514/812
[58] Field of Search ........................................ 514/392

[56] References Cited

U.S. PATENT DOCUMENTS

| 3,342,826 | 9/1967 | Miller et al. | 546/224 |
| 4,210,660 | 7/1980 | Takashima et al. | 514/426 |
| 4,835,172 | 5/1989 | Acker et al. | 514/392 |
| 4,887,780 | 10/1989 | Vega-Noverola et al. | 514/161 |

OTHER PUBLICATIONS

Drugs, vol. 25, pp. 463–464 (1983).
Pharmacology Biochemistry & Behavior, vol. 15, pp. 695–699 (1981).
Neuropharmacology, vol. 26, No. 2/3, pp. 195–200 (1987).
Annals of the New York Academy of Sciences, vol. 95, pp. 315–335 (1962).
Pharmacology Biochemistry & Behavior, vol. 32, pp. 777–785 (1989).

Primary Examiner—Frederick E. Waddell
Assistant Examiner—T. J. Criares
Attorney, Agent, or Firm—Fitzpatrick, Cella, Harper & Scinto

[57] ABSTRACT

Anxiolytic and antipsychotic treatment is provided to patients by administering therapeutically effective amounts of N-[2-(diethylamino)-ethyl]-2-methoxy-4-[(1-H-4,5-dihydro-2-immidazolyl)-amino]-5-chlorobenzamide, or a pharmaceutically acceptable salt thereof.

4 Claims, 9 Drawing Sheets

METHOD OF PROVIDING ANXIOLYTIC AND ANTIPSYCHOTIC TREATMENT

BACKGROUND OF THE INVENTION

A number of common physical, mental and psychological disorders have been associated with states of psychoneuroses or anxiety. Such states typically result in feelings of apprehension, uncertainty or fear, without apparent stimulus or objectively out of proportion to any apparent cause, and may be associated with physiological changes such as tachycardia, sweating and tremors. Furthermore, an extreme state of anxiety is a common consequence of withdrawal from substances capable of inducing drug dependence, such as alcohol, nicotine and cocaine. In use, such substances produce an anxiolytic effect. However, their chronic use is accompanied by a state of dependence. The sudden interruption of these substances may even exacerbate the initial anxiety, making withdrawal from the substances extremely difficult.

The benzodiazepine-type drugs customarily used in the treatment of anxiety have the disadvantage of inducing, on cessation of treatment, an exacerbation of the anxiety and, therefore, do not constitute effective therapy, for instance, for drug addicts undergoing withdrawal. Accordingly, chemical compounds that can relieve states of psychoneuroses or anxiety have been sought for use as pharmaceutical agents in the treatment of patients. In particular, there has been a need for anxiolytic agents that relieve the anxiety of withdrawal from addictive drug substances.

Schizophrenia is an imbalance that encompasses any of a group of severe emotional disorders, usually of psychotic proportions, characterized by misinterpretation and retreat from reality, delusions, hallucinations, ambivalence, inappropriate affect, and withdrawn, bizarre, or regressive behavior. Accordingly, chemical compounds that can relieve the anxiety characteristic of psychotic disorders such as schizophrenia have also been sought for use as pharmaceutical agents in the treatment of patients.

The present theory of the physiopathology of schizophrenia is that an augmented dopaminergic activity in the medial temporal lobes of the brain is responsible for the dopamine induced hyperactivity characteristic of this disorder. Thus, the antipsychotic drugs currently in use are antidopaminergics.

SUMMARY OF THE INVENTION

The present invention concerns pharmaceutical uses of the compound N-[2-(diethylamino)-ethyl]-2-methoxy-4-[(1H-4,5-dihydro-2-imidazolyl)-amino]-5-chlorobenzamide, represented by the following chemical structure:

or any of the pharmaceutically acceptable salts thereof (herein referred to as "The Compound").

The Compound, and methods for its preparation, are described in French Patent No. 2592042 and U.S. Pat. No. 4,835,172, issued May 30, 1989, the disclosures of which are incorporated herein by references, as an activator of the central nervous system and antidepressant. The antidepressant activity has been confirmed by Porsolt's test, a conventional and known protocol well-accepted in the art.

In addition to such properties, it has now been found that The Compound possesses anxiolytic and antipsychotic properties.

The Compound has been shown to be a potent anxiolytic agent in standard laboratory animals. This has been demonstrated by the two-compartment (dark and light) box test in the mouse, by observation of "social" behavior of the rat and by the human confrontation test in the marmoset. Furthermore, The Compound relieves the anxiety of withdrawal from substances capable of inducing drug dependence without causing the anxiety-generating effects manifested on the cessation of chronic treatment with conventional anxiolytic agents of the benzodiazepine-type.

As a psychotropic agent, The Compound is distinguished from other methoxybenzamide compounds by the fact that it does not possess antidopaminergic properties. Thus, The Compound is not a neuroleptic in the usual sense of the term, as it is not bound to the $D_1$-$D_2$ dopaminergic receptors. It is inactive in the behavior tests customarily performed to test neuroleptics. These results do not suggest that The Compound is an antipsychotic agent. However, the tests conducted have demonstrated that The Compound does suppress the hyperactivity induced by dopamine perfused in the brain of the rat, more specifically in the nucleus accumbens, thus indicating a utility in the treatment of psychotic disorders such as schizophrenia.

DETAILED DESCRIPTION OF THE INVENTION

A very thorough study of The Compound in standard laboratory animals has demonstrated that it possesses unexpected properties. The protocols used and the test results obtained are described hereinafter.

TWO-COMPARTMENT BOX TEST IN THE MOUSE

This test is based on a natural aversion of mice to light. The apparatus used is a box containing two compartments, one of which is dark (labeled "black compartment" in the figures) and the other illuminated (labeled "white compartment" in the figures). The apparatus is designed to allow the animal to choose between staying in either of the two compartments. Under normal conditions, the mice avoid light and remain especially in the dark compartment. Under the influence of an anxiolytic agent, however, exploration of the illuminated compartment predominates.

The test consists of placing each mouse in the center of the illuminated compartment and observing the animal's behavior by video system for 5 minutes. The number of exploratory rearings and the number of displacements (the crossing of lines traced on the floor of each compartment constitute "passages") are then recorded for each compartment.

An anxiolytic effect induced by a drug such as diazepam is characterized by an increase in the number of exploratory rearings and in the number of passages into the illuminated compartment.

According to the results shown in FIGS. 1A-2D, The Compound exerts an anxiolytic effect in this test which is manifested at 0.001 mg/kg subcutaneously and 0.1 mg/kg orally by a significant increase in the number of exploratory rearings and displacements into the illuminated compartment.

"SOCIAL" BEHAVIOR TEST IN THE RAT

This test consists of observing by video system the behavior of 2 rats, coming from different cages, brought into each other's presence for 10 minutes in a brightly illuminated box.

The "social" behavior of each animal is assessed by measurement of the duration of different activities: smelling the partner, leaping over the partner, grooming, genital exploration and shadowing of the partner. Under the anxiety-generating influence of light, such behavior tends to be maintained at a reduced level.

The administration of anxiolytic substances such as benzodiazepines tends to lift that effect with, consequently, an enhancement of social behavior.

Figure 1A:
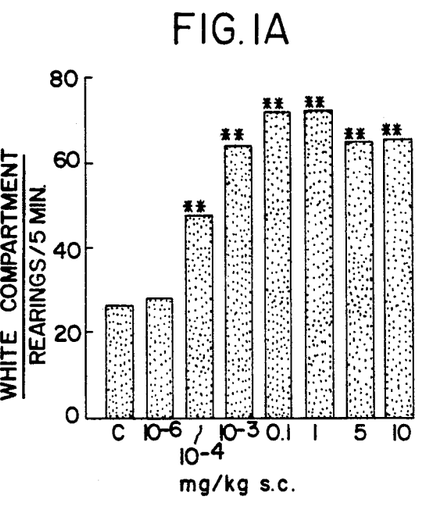
FIGS. 1A-1D illustrate graphically the anxiolytic activity of The Compound when administered subcutaneously in the mouse using the 2-compartment box test.
Figure 1B:
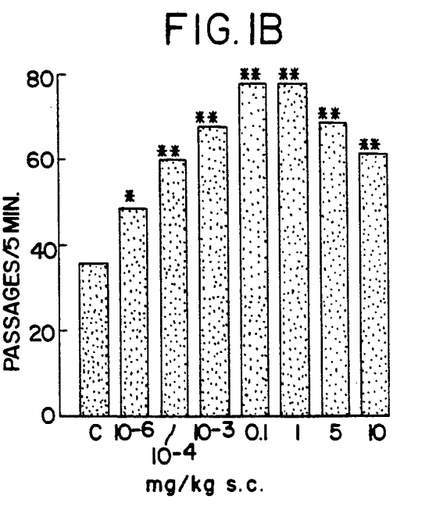
Figure 1C:
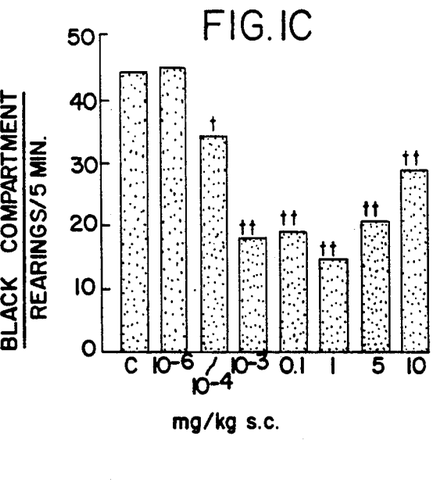
Figure 1D:
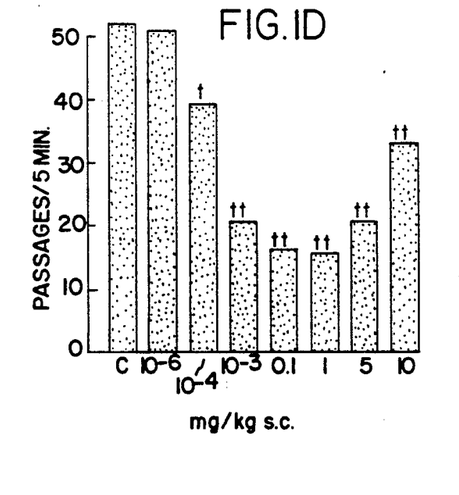
Figure 2A:
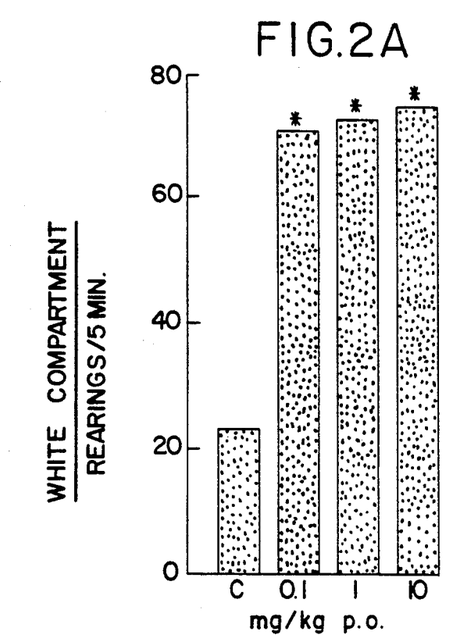
FIGS. 2A-2D illustrate graphically the anxiolytic activity of The Compound when administered orally in the mouse using the 2-compartment box test.
Figure 2B:
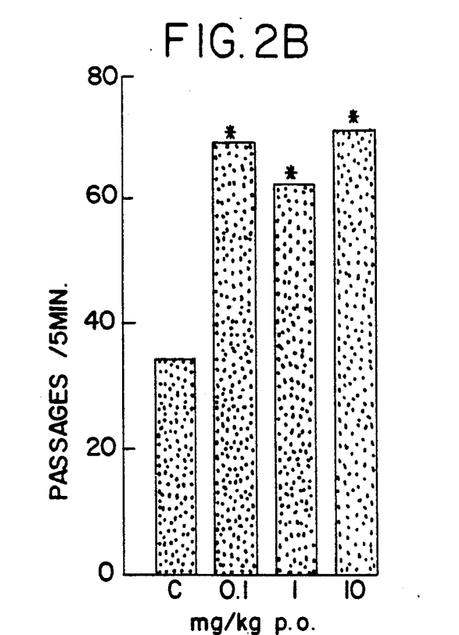
Figure 2C:
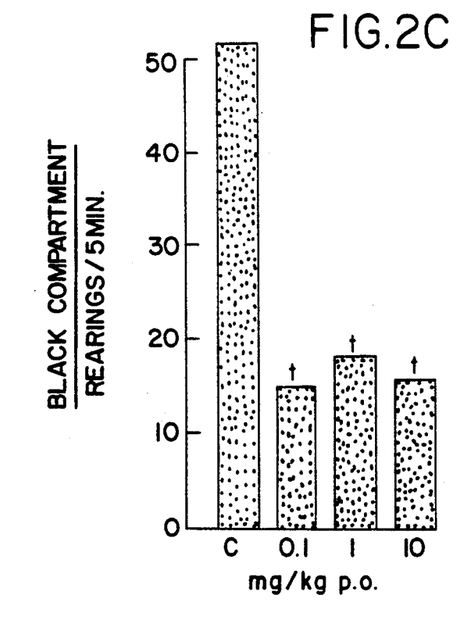
Figure 2D:
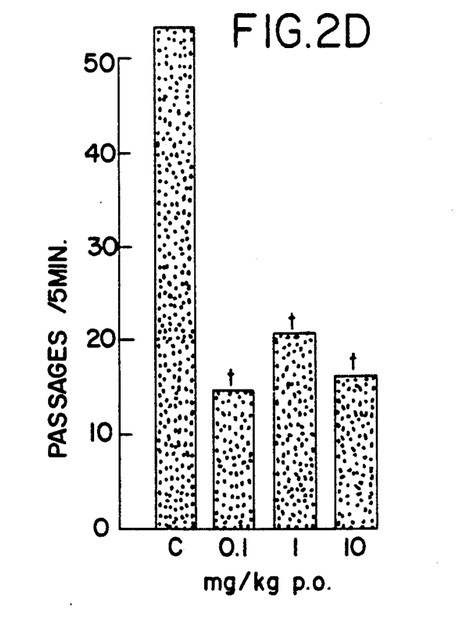
Figure 3:
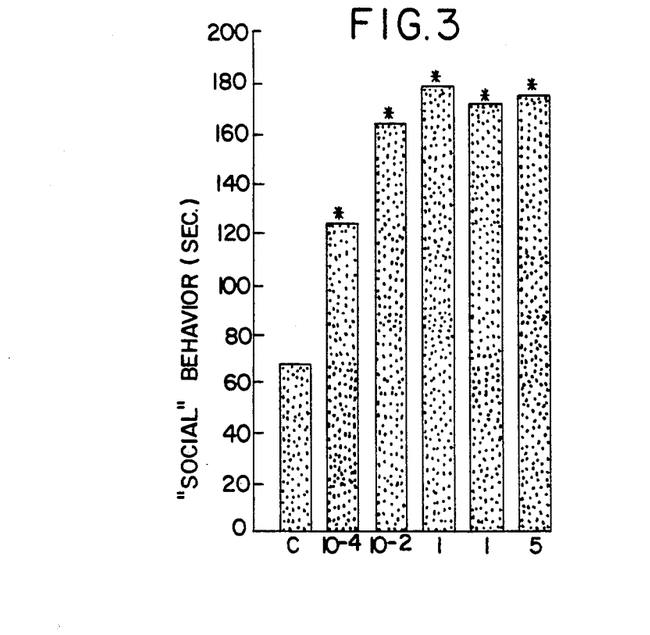
FIG. 3 illustrates graphically the anxiolytic action of The Compound in a social behavior model in the rat.

According to the results shown in FIG. 3, The Compound enhances social behavior in a statistically significant manner after the subcutaneous administration of a minimal dose of 0.0001 mg/kg.

ANXIETY TEST IN THE MARMOSET

In the marmoset, the presence of an unknown experimentor standing 60 cm from the animal's cage triggers anxiety, which is manifested by a series of aggressive postures and the animal's retreat to the back of the cage.

The administration of an anxiolytic substance like diazepam, for example, reduces the animal's anxiety and one observes a diminution of the number of aggressive postures as well as an increase in the time spent in front of the cage facing the experimentor.

Figure 4A:
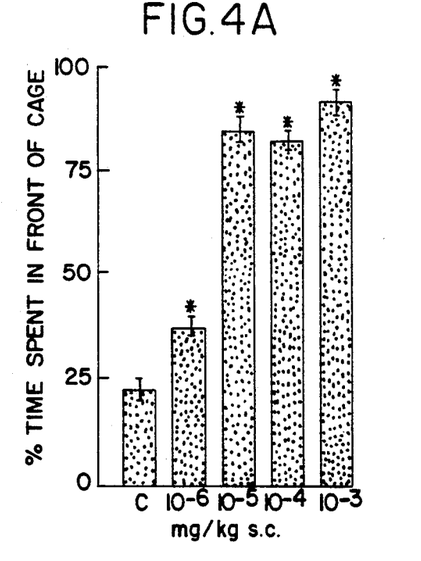
FIGS. 4A and 4B illustrate graphically the anxiolytic action of The Compound in the marmoset confronted with human presence.
Figure 4B:
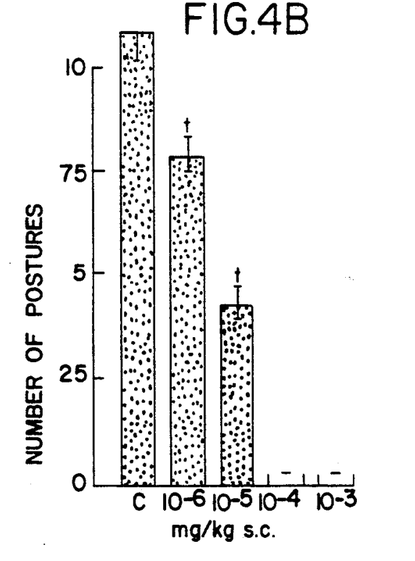
Figure 5A:
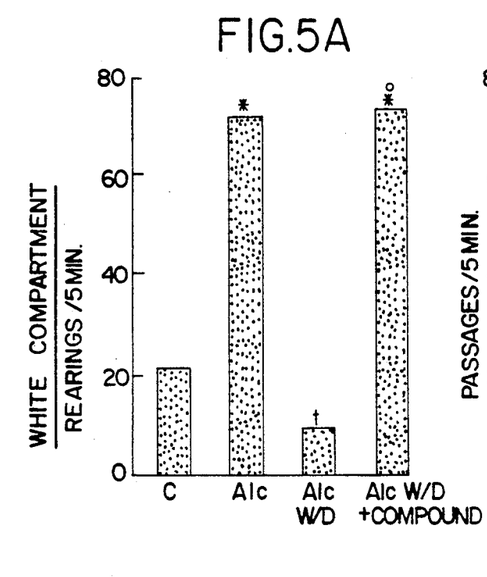
FIGS. 5A-5D illustrate graphically the antagonism to anxiety generated by withdrawal from alcohol by The Compound.
Figure 5B:
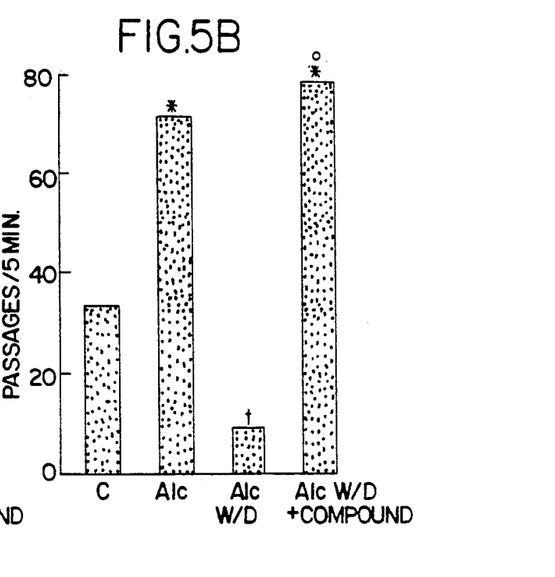
Figures 5C, 5D:
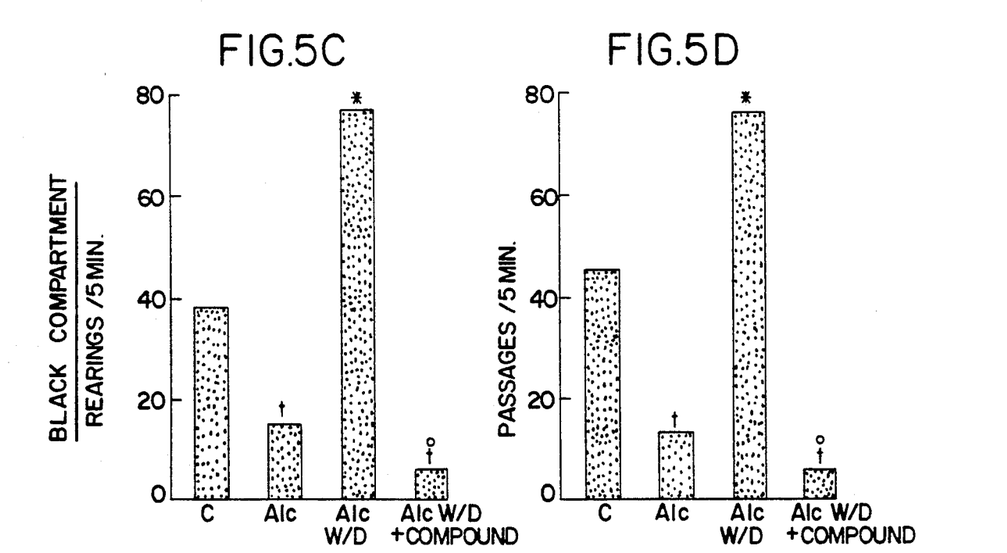

The Compound likewise reduces anxiety. According to the results shown in FIGS. 4A and 4B, the anxiolytic effect is manifested subcutaneously at from 0.000001 mg/kg by a significant diminution in the number of aggressive postures and a significant increase in the time spent in front of the cage.

ANXIETY INDUCED BY WITHDRAWAL

Mice rendered dependent by the repeated administration of various substances undergo withdrawal upon cessation of treatment. The anxiety induced by such withdrawal is objectively represented, as previously described, by the two-compartment box test.

In general, the administration of substances inducing dependence diminishes the animal's "anxiety state" which is expressed by an increase in the number of rearings and passages into the illuminated compartment. On withdrawal, one encounters an exacerbation of the animal's anxiety with a consequent increase in the number of rearings and passages into the dark compartment which exceed the values observed before administration of the substance.

The test consists of administering the substance to be tested on withdrawal until the day of the two-compartment box test. The increase in the number of passages and rearings in the illuminated compartment is the criterion of effectiveness of the substance on withdrawal-induced anxiety. The Compound has reduced the anxiety induced by withdrawal of alcohol, nicotine and cocaine in this test.

ALCOHOL DEPENDENCE

Mice rendered alcohol-dependent by the addition of 8% alcohol to the drinking water for 14 days undergo withdrawal and are tested 48 hours after the start of withdrawal; i.e., the time when maximum anxiety-generating effects are manifested.

According to the results shown in FIGS. 5A-5D, the subcutaneous administration of 1 mg/kg/day of The Compound for 48 hours after withdrawal significantly increases the number of passages and of rearings in the illuminated compartment by comparison with the untreated withdrawn animals.

NICOTINE DEPENDENCE

Mice rendered nicotine-dependent by the intraperitoneal administration of 0.1 mg/kg twice-daily of nicotine for 14 days undergo withdrawal and are tested 48 hours after the start of withdrawal; i.e., the time when maximum anxiety-generating effects are manifested.

Figure 6A:
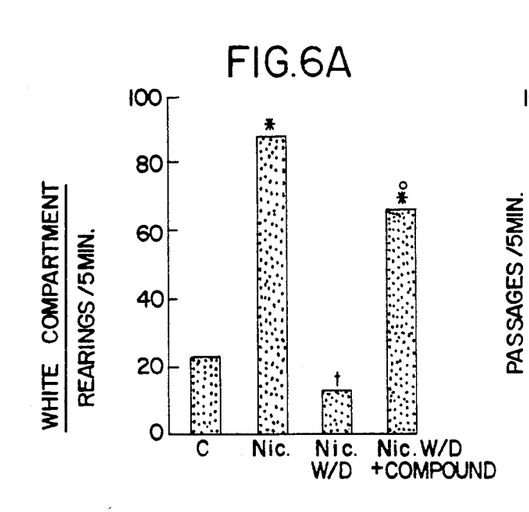
FIGS. 6A-6D illustrate graphically the antagonism to anxiety generated by withdrawal from nicotine by The Compound.
Figure 6B:
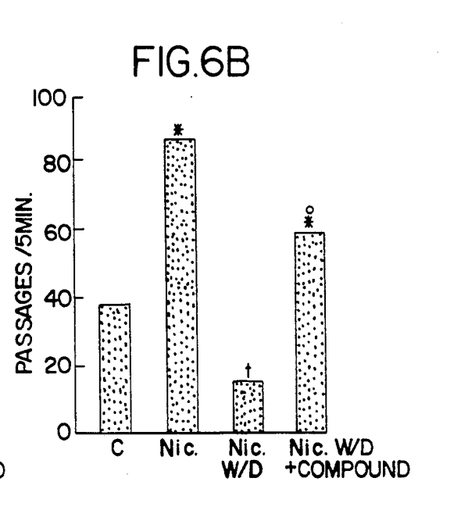
Figure 6C:
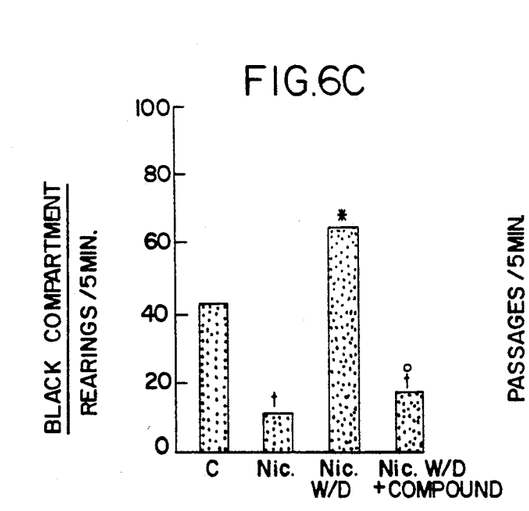
Figure 6D:
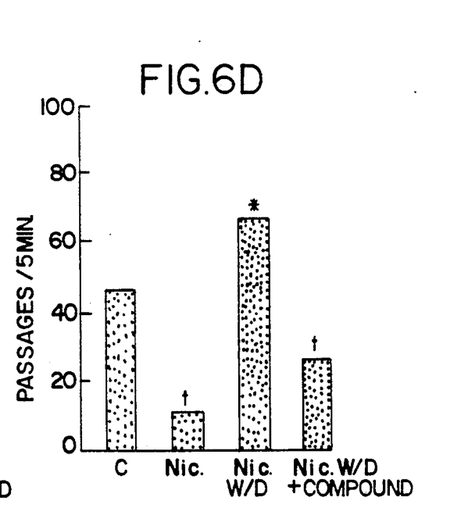
Figure 7A:
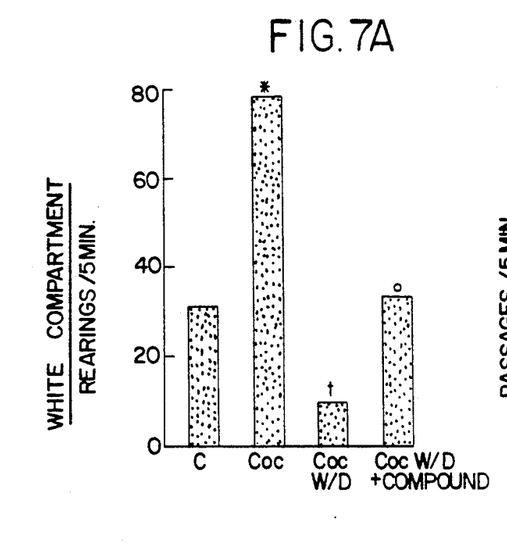
FIGS. 7A-7D illustrate graphically the antagonism to anxiety generated by withdrawal from cocaine by The Compound.
Figure 7B:
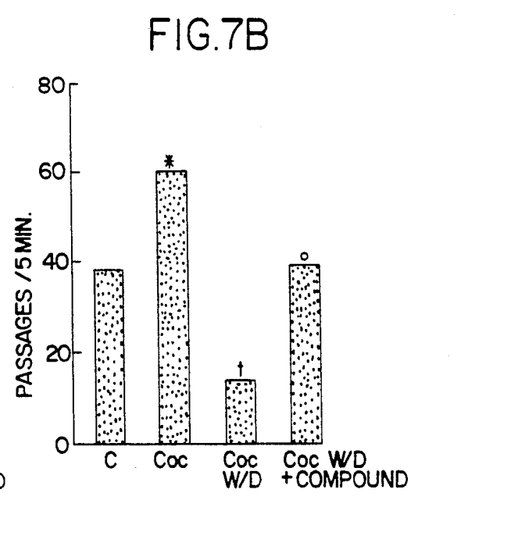
Figure 7C:
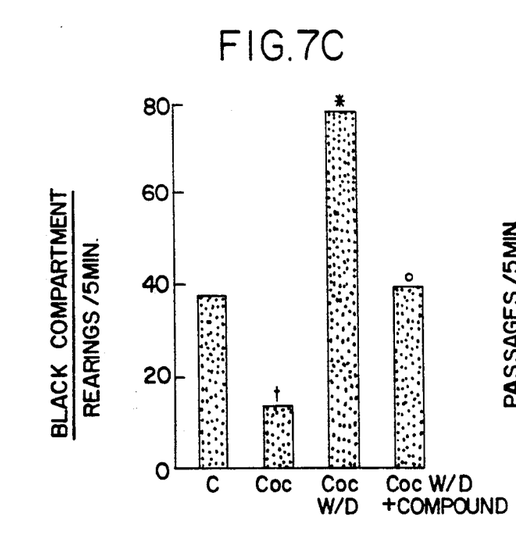
Figure 7D:
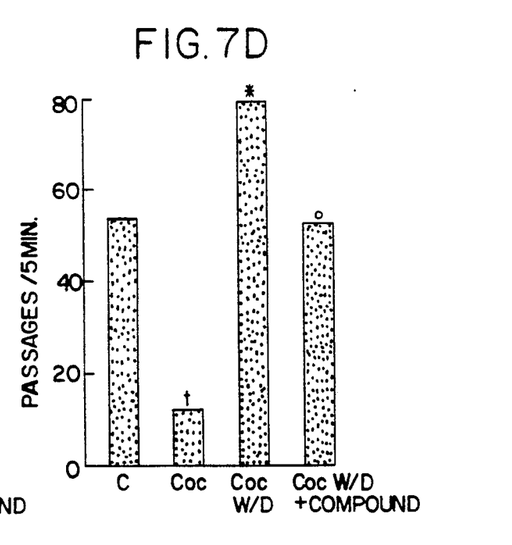
Figure 8A:
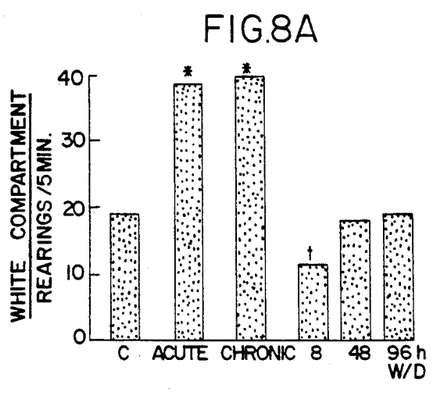
FIGS. 8A-8D illustrate graphically the effect of withdrawal after chronic treatment with a benzodiazepine in the mouse using the 2-compartment box test.
Figure 8B:
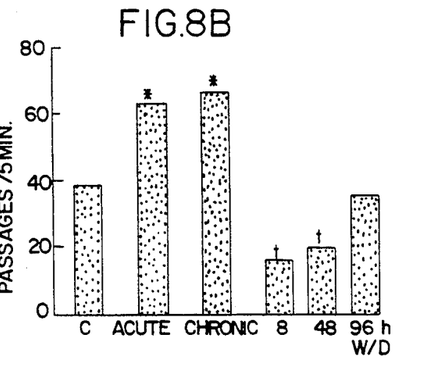
Figure 8C:
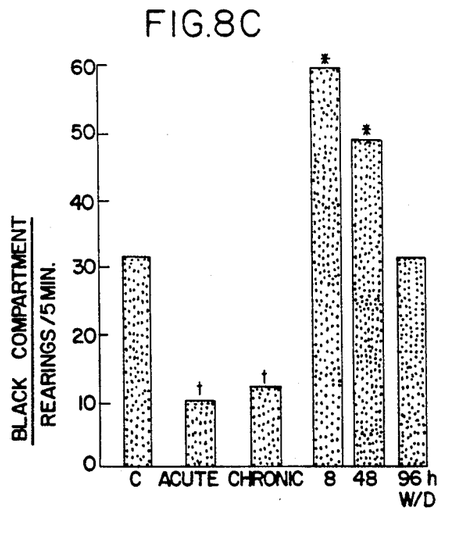
Figure 8D:
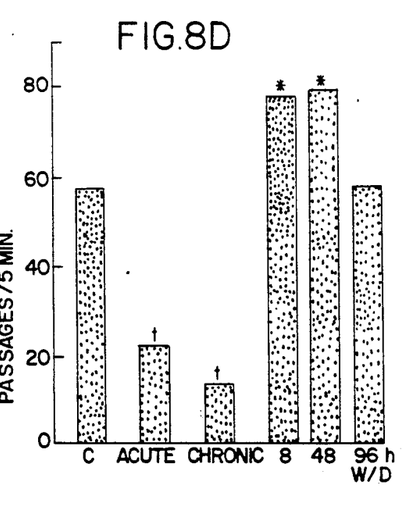
Figure 9A:
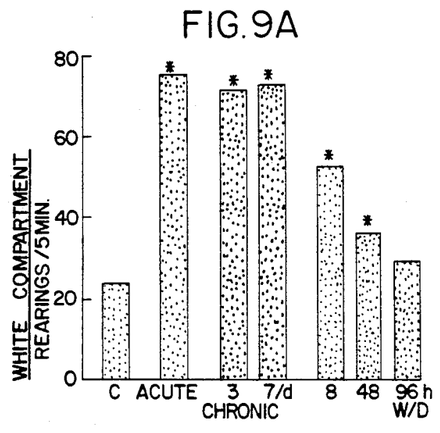
FIGS. 9A-9D illustrate graphically the effect of withdrawal after chronic treatment with The Compound in the mouse using the 2-compartment box test.
Figure 9B:
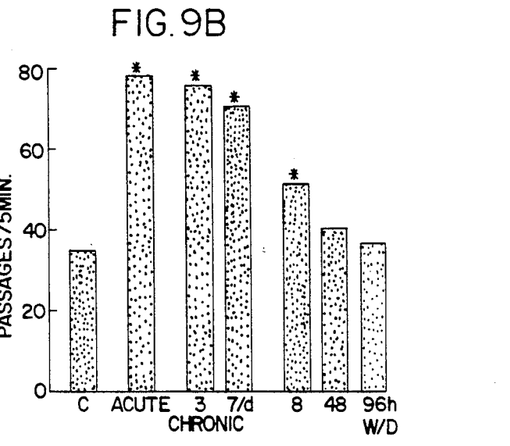
Figure 9C:
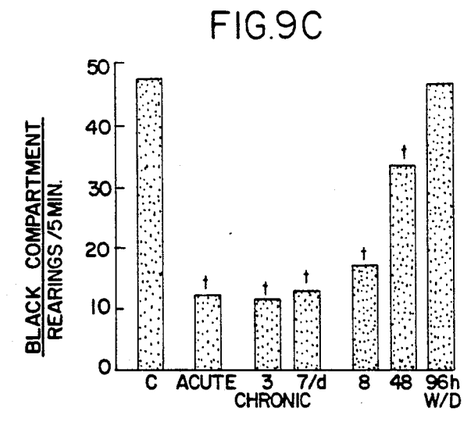
Figure 9D:
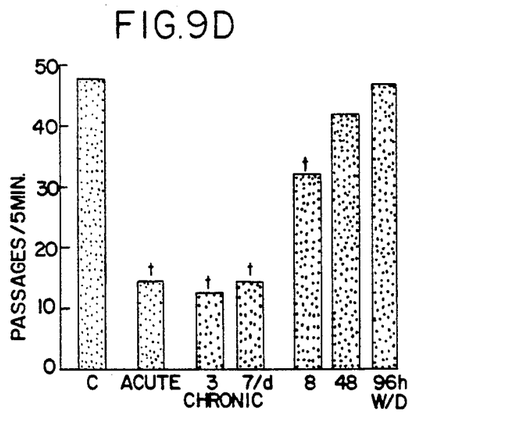

According to the results shown in FIGS. 6A-6B, the subcutaneous administration of 1 mg/kg/day of The Compound for 48 hours after withdrawal significantly increases the number of passages and of rearings in the illuminated compartment by comparison with the untreated withdrawn animals.

COCAINE DEPENDENCE

Mice rendered cocaine-dependent by the administration of 1 mg/kg twice-daily for 14 days undergo withdrawal and are tested 8 hours after the start of withdrawal; i.e., the time when maximum anxiety-generating effects are manifested. According to the results shown in FIGS. 7A-7D, the subcutaneous administration at the start of withdrawal of 1 mg/kg of The Compound significantly increases the number of passages and of rearings in the illuminated compartment by comparison with the untreated withdrawn animals.

INVESTIGATION OF WITHDRAWAL ANXIETY GENERATED WITH THE COMPOUND EMPLOYED IN THE METHODS OF THE INVENTION, COMPARED TO THAT INDUCED BY BENZODIAZEPINES

Some substances, such as benzodiazepines, induce a dependence after chronic use, which is one of the disadvantages of therapy with such substances. As reflected by the results shown in FIGS. 8A-8D, the chronic administration of a benzodiazepine for 7 days entails after the cessation of treatment a recrudescence of anxiety, objectively manifested by an increased number of rearings and of passages into the dark compartment.

According to the results shown in FIGS. 9A-9D, the chronic subcutaneous administration of The Compound at a dose of 1 mg/kg twice-daily for 7 days does not induce anxiety within 8, 48 or 96 hours after the cessation of treatment. On the other hand, it is observed that the anxiolytic effect of The Compound is maintained after withdrawal, as the rearings and passages into the illuminated compartment remain significantly greater than those of the controls 8 and 48 hours after withdrawal, before returning to the control values in 96 hours.

HYPERACTIVITY INDUCED BY PERFUSION OF DOPAMINE INTO THE NUCLEUS ACCUMBENS IN THE RAT

One of the factors mentioned to explain the genesis of schizophrenia is a cerebral dopaminergic hyperactivity. The suppression of such hyperactivity, as with neuroleptics, would make possible an improvement of the psychotic state.

In the hyperactivity test in the rat, dopamine is perfused by the intracerebral route into the nucleus accumbens by means of osmotic minipumps at a dose of 24 $\mu$g/24 hours for 13 days. The spontaneous motor activity of the rats placed in individual cages is measured by means of photoelectric cells. The results are expressed in the number of interruptions of light beams corresponding to the photoelectric cells (passage of the animal).

On the administration of dopamine, an increase of locomotor activity of the animals is observed, manifested by two peaks in hyperactivity toward the 3rd and 9th days. The standard neuroleptics prevent occurrence of that hyperactivity when they are administered during the period of perfusion.

Figure 10A:
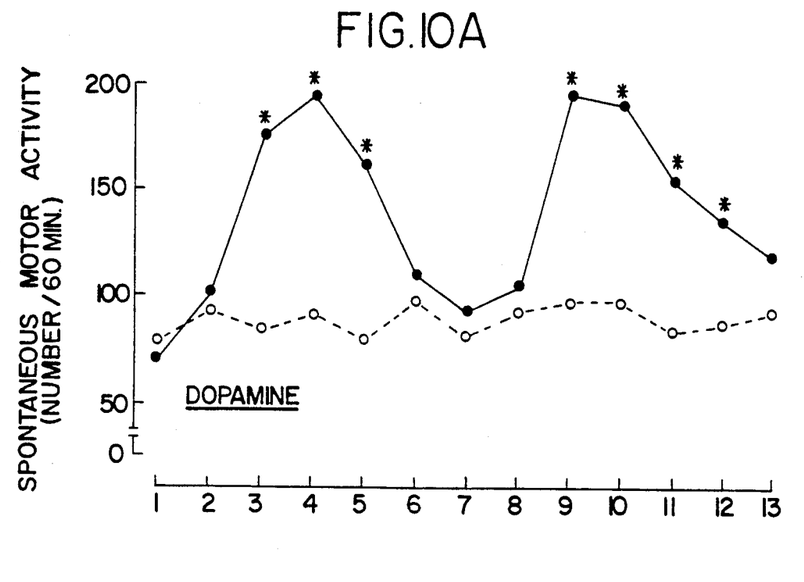
FIGS. 10A and 10B illustrate graphically the antagonism by The Compound to the hyperactivity induced by dopamine perfused bilaterally in the nucleus accumbens of the rat.
Figure 10B:
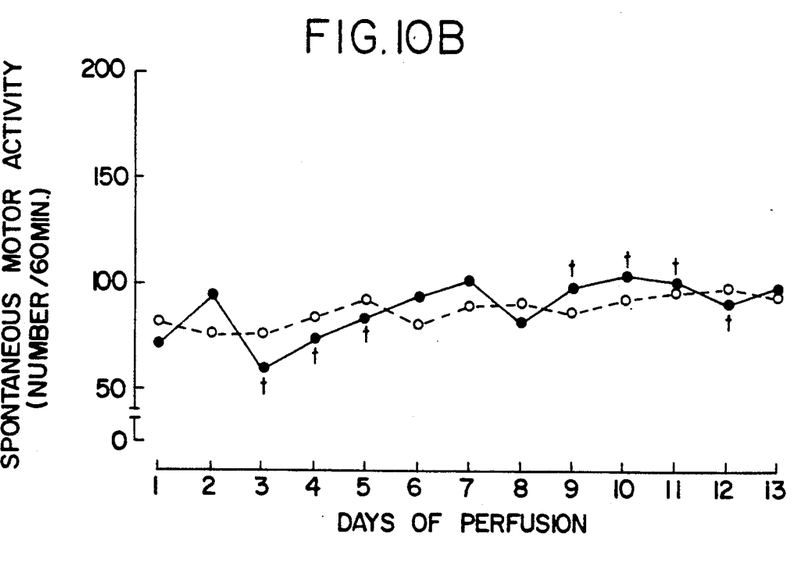

According to the results shown in FIGS. 10A and 10B, the subcutaneous administration of The Compound at a dose of 0.01 mg/kg twice-daily prevents occurrence of the hyperactivity normally induced by the perfusion of dopamine.

The foregoing tests demonstrate the anxiolytic and antipsychotic activity of The Compound and its utility for the treatment of various anxiety states, as well for the treatment of certain psychotic states. Furthermore, the test results evidence the usefulness of The Compound in facilitating withdrawal from substances and medications capable of creating drug dependence by forestalling the anxiety generated by their interruption.

Thus, The Compound may be administered in therapeutically effective amounts to patients including lower animals and humans.

The Compound can be administered in any number of conventional pharmaceutical forms including, but not limited to, tablets, capsules, pills, syrups, injectable solutions or other dosage forms intended for oral, parenteral or any other conventional pharmaceutical administration, in combination with solid or liquid excipients. Substances which are inert relative to The Compound can be used in these preparations, such as lactose, magnesium stearate, starch, talc, cellulose, levilite, alkali metal lauryl-sulphates, saccharose and other vehicles commonly employed in pharmaceutical preparations.

By way of illustration only, The Compound may be formulated in tablet dosage form as shown below. As the formulation is provided for illustrative purposes only, it is understood that the invention is not restricted or limited thereto, as the scope of the invention is defined and restricted or limited solely as set forth in the appended claims.

| | |
|---|---|
| N-[2-(diethylamino)-ethyl]-2-methoxy-4-[(1-H-4,5-dihydro-2-imidazolyl)-amino]-5-chlorobenzamide | 100 mg |
| dried starch | 20 mg |
| lactose | 100 mg |
| methylcellulose 1500 cps | 1.5 mg |
| levilite | 10 mg |
| magnesium stearate | 4 mg |

What is claimed is:

1. A method of treating anxiety which comprises administering to a patient exhibiting anxiety characteristics a therapeutically effective amount of N-[2-(diethylamino)-ethyl]-2-methoxy-4-[(1-H-4,5-dihydro-2-imidazolyl-amino]-5-chlorobenzamide, or a pharmaceutically acceptable salt thereof.

2. A method of treating anxiety caused by withdrawal from alcohol which comprises administering to a patient exhibiting anxiety characteristics due to said withdrawal from alcohol a therapeutically effective amount of N-[2-(diethylamino)-ethyl]-2-methoxy-4-[(1-H-4,5-dihydro-2-imidazolyl-amino]-5-chlorobenzamide, or a pharmaceutically acceptable salt thereof.

3. A method of treating anxiety caused by withdrawal from nicotine which comprises administering to a patient exhibiting anxiety characteristics due to said withdrawal from nicotine a therapeutically effective amount of N-[2-(diethylamino)-ethyl]-2-methoxy-4-[(1-H-4,5-dihydro-2-imidazolyl-amino]-5-chlorobenzamide, or a pharmaceutically acceptable salt thereof.

4. A method of treating anxiety caused by withdrawal from cocaine which comprises administering to a patient exhibiting anxiety characteristics due to said withdrawal from cocaine a therapeutically effective amount of N-[2-(diethylamino)-ethyl]-2-methoxy-4-[(1-H-4,5-dihydro-2-imidazolyl-amino]-5-chlorobenzamide, or a pharmaceutically acceptable salt thereof.

* * * * *

UNITED STATES PATENT AND TRADEMARK OFFICE
CERTIFICATE OF CORRECTION

PATENT NO. : 5,116,859
DATED : May 26, 1992
INVENTOR(S) : JACQUES ACHER, ET AL.

It is certified that error appears in the above-identified patent and that said Letters Patent is hereby corrected as shown below:

Title page:

IN [56] REFERENCES CITED

Under U.S. PATENT DOCUMENTS, "Acker et al." should read --Acher et al.--.

IN [57] ABSTRACT

Line 4, "2-immidazolyl)" should read --2-imidazolyl)--.

COLUMN 2

Line 20, "references" should read --reference--.

Signed and Sealed this

Seventh Day of September, 1993

Attest:

BRUCE LEHMAN

Attesting Officer        Commissioner of Patents and Trademarks